United States Patent
Prinstil et al.

(10) Patent No.: US 8,601,867 B2
(45) Date of Patent: Dec. 10, 2013

(54) MAGNETOSTRICTIVE PROBE HAVING PHASE SEPARATION FLOAT ASSEMBLY

(75) Inventors: Ambroise Prinstil, East Hartford, CT (US); Joseph Tessitore, Winston-Salem, NC (US)

(73) Assignee: Veeder-Root Company, Simsbury, CT (US)

( * ) Notice: Subject to any disclaimer, the term of this patent is extended or adjusted under 35 U.S.C. 154(b) by 48 days.

(21) Appl. No.: 13/191,194

(22) Filed: Jul. 26, 2011

(65) Prior Publication Data

US 2012/0152016 A1   Jun. 21, 2012

Related U.S. Application Data

(60) Provisional application No. 61/367,677, filed on Jul. 26, 2010.

(51) Int. Cl.
| | |
|---|---|
| *G01F 23/00* | (2006.01) |
| *G01F 23/30* | (2006.01) |
| *G01F 23/40* | (2006.01) |
| *G01F 23/76* | (2006.01) |

(52) U.S. Cl.
USPC ............ 73/311; 73/290 R; 73/305; 73/306; 73/64.55; 73/DIG. 2; 73/DIG. 5; 73/322.5

(58) Field of Classification Search
USPC ........................................... 73/311
See application file for complete search history.

(56) References Cited

U.S. PATENT DOCUMENTS

| | | | |
|---|---|---|---|
| 1,340,293 A | | 5/1920 | Roach et al. |
| 2,458,759 A | * | 1/1949 | Abell, Jr. ................. 73/752 |
| 3,794,913 A | | 2/1974 | Cropper et al. |

(Continued)

FOREIGN PATENT DOCUMENTS

| | | |
|---|---|---|
| EP | 1992920 A1 | 11/2008 |
| GB | 937713 A | 9/1963 |

(Continued)

OTHER PUBLICATIONS

PCT International Search Report and Written Opinion of the International Searching Authority dated Dec. 12, 2011 for PCT/US2011/45382 filed on Jul. 26, 2011, corresponding to co-pending U.S. Appl. No. 13/191,194.

(Continued)

*Primary Examiner* — Leonard Chang
*Assistant Examiner* — Irving A Campbell
(74) *Attorney, Agent, or Firm* — Nelson Mullins Riley & Scarborough LLP

(57) ABSTRACT

Embodiments of the present invention provide a phase separation float assembly, a phase separation detection system, and a method for detecting phase separation. One embodiment comprises a first float subassembly comprising a first float adapted for vertical travel along a fuel level probe shaft and a magnet. This embodiment also comprises a second float subassembly comprising a second float adapted for vertical travel along the shaft. The first float has a first density and the second float has a second density greater than the first density. The second float subassembly further comprises at least one stop feature which engages the first float subassembly when the first float subassembly travels vertically a predetermined distance along the fuel level probe shaft. The first float density is selected such that the first float subassembly travels vertically along the shaft to engage the at least one stop feature in the presence of phase separation.

50 Claims, 12 Drawing Sheets

(56) References Cited

U.S. PATENT DOCUMENTS

| | | | |
|---|---|---|---|
| 3,862,571 A | 1/1975 | Vogel | |
| 3,935,741 A * | 2/1976 | Zinsmeyer et al. | 73/313 |
| 3,946,625 A | 3/1976 | Miyazaki et al. | |
| 4,155,254 A * | 5/1979 | Colditz | 73/447 |
| 4,166,244 A | 8/1979 | Woods et al. | |
| 4,176,553 A | 12/1979 | Wood | |
| 4,178,623 A | 12/1979 | Emmerich et al. | |
| 4,194,395 A | 3/1980 | Wood | |
| 4,349,882 A | 9/1982 | Asmundsson et al. | |
| 4,397,183 A | 8/1983 | Ballou et al. | |
| 4,594,892 A | 6/1986 | Asmundsson | |
| 4,600,844 A | 7/1986 | Atkins | |
| 4,672,842 A * | 6/1987 | Hasselmann | 73/49.2 |
| 4,679,433 A | 7/1987 | Clinton et al. | |
| 4,706,203 A | 11/1987 | Ramsdale et al. | |
| 4,720,997 A | 1/1988 | Doak et al. | |
| 4,728,924 A | 3/1988 | Franklin | |
| 4,789,946 A | 12/1988 | Sinz | |
| 4,885,529 A | 12/1989 | Lee et al. | |
| 4,972,710 A | 11/1990 | Uhlarik et al. | |
| 4,977,528 A | 12/1990 | Norris | |
| 5,068,617 A | 11/1991 | Reich | |
| 5,076,100 A | 12/1991 | Hunter et al. | |
| 5,089,783 A | 2/1992 | Kapsokavathis et al. | |
| 5,129,261 A | 7/1992 | Riley | |
| 5,138,880 A | 8/1992 | Lee et al. | |
| 5,142,909 A | 9/1992 | Baughman | |
| 5,189,911 A | 3/1993 | Ray et al. | |
| 5,253,522 A | 10/1993 | Nyce et al. | |
| 5,319,545 A | 6/1994 | McGarvey et al. | |
| 5,400,253 A | 3/1995 | O'Connor | |
| 5,406,838 A | 4/1995 | Miller | |
| 5,423,214 A | 6/1995 | Lee | |
| 5,423,457 A | 6/1995 | Nicholas et al. | |
| 5,471,873 A | 12/1995 | Nyce et al. | |
| 5,602,333 A | 2/1997 | Larrabee et al. | |
| 5,722,469 A * | 3/1998 | Tuminaro | 141/94 |
| 5,734,851 A | 3/1998 | Leatherman et al. | |
| 5,956,259 A | 9/1999 | Hartsell, Jr. et al. | |
| 6,016,697 A | 1/2000 | McCulloch et al. | |
| 6,052,629 A | 4/2000 | Leatherman et al. | |
| 6,058,775 A | 5/2000 | Levy | |
| 6,269,694 B2 | 8/2001 | Morimoto | |
| 6,278,281 B1 | 8/2001 | Bauer et al. | |
| 6,318,152 B1 | 11/2001 | Hagihara et al. | |
| 6,433,560 B1 | 8/2002 | Hansen et al. | |
| 6,481,277 B1 * | 11/2002 | Wakamiya et al. | 73/311 |
| 6,519,539 B1 | 2/2003 | Freeman et al. | |
| 6,578,416 B1 | 6/2003 | Vogel et al. | |
| 6,624,755 B1 | 9/2003 | Chamberlin | |
| 6,693,444 B2 | 2/2004 | Lin et al. | |
| 6,782,736 B1 | 8/2004 | Hammer | |
| 6,918,296 B1 | 7/2005 | Urquidi et al. | |
| 6,938,478 B2 | 9/2005 | Arias | |
| 7,278,311 B1 * | 10/2007 | Demin | 73/322.5 |
| 7,360,418 B2 | 4/2008 | Pelovitz | |
| 7,403,860 B2 | 7/2008 | Hart | |
| 7,441,455 B2 | 10/2008 | Vargas Da Silva | |
| 7,454,969 B2 * | 11/2008 | Hart | 73/306 |
| 7,473,352 B2 | 1/2009 | Sundeng | |
| 7,659,731 B2 | 2/2010 | Lin et al. | |
| 2001/0020383 A1 | 9/2001 | Moos et al. | |
| 2003/0057968 A1 | 3/2003 | Wang et al. | |
| 2003/0185715 A1 | 10/2003 | Krivts et al. | |
| 2004/0003660 A1 * | 1/2004 | Fukuhara et al. | 73/319 |
| 2004/0093943 A1 | 5/2004 | Arias | |
| 2006/0169039 A1 | 8/2006 | Zalenski et al. | |
| 2006/0181262 A1 | 8/2006 | Glenn et al. | |
| 2006/0248952 A1 | 11/2006 | Jarvie | |
| 2007/0180904 A1 | 8/2007 | Gao | |
| 2008/0053202 A1 | 3/2008 | Rohklin et al. | |
| 2008/0230146 A1 | 9/2008 | Kastner et al. | |
| 2009/0126481 A1 | 5/2009 | Burris | |
| 2009/0173698 A1 | 7/2009 | Sundeng | |
| 2009/0217753 A1 | 9/2009 | Burris | |
| 2009/0265132 A1 | 10/2009 | Schrittenlacher et al. | |
| 2010/0170338 A1 | 7/2010 | Prinstil et al. | |
| 2010/0295565 A1 | 11/2010 | Drack | |
| 2011/0048125 A1 | 3/2011 | Jackson et al. | |
| 2011/0090088 A1 | 4/2011 | Kenney et al. | |
| 2011/0185794 A1 | 8/2011 | Moss | |
| 2012/0155504 A1 | 6/2012 | Jarvie et al. | |
| 2012/0261437 A1 | 10/2012 | Sabo et al. | |

FOREIGN PATENT DOCUMENTS

| | | |
|---|---|---|
| JP | 57-008434 A | 1/1982 |
| JP | 2007-239510 A | 9/2007 |
| JP | 2010-030623 A | 2/2010 |
| WO | 2008/064010 A2 | 5/2008 |
| WO | 2008104967 A2 | 9/2008 |
| WO | 2009089339 A2 | 7/2009 |

OTHER PUBLICATIONS

Machine translation of European Pub. No. 1992920A1 published on Nov. 19, 2008.

English language Abstract of Japanese Pub. No. 2007-239510 published on Sep. 20, 2007.

English language Abstract of Japanese Pub. No. 2010-030623 published on Feb. 12, 2010.

English language Abstract of Japanese Pub. No. 57-008434 published on Jan. 16, 1982.

* cited by examiner

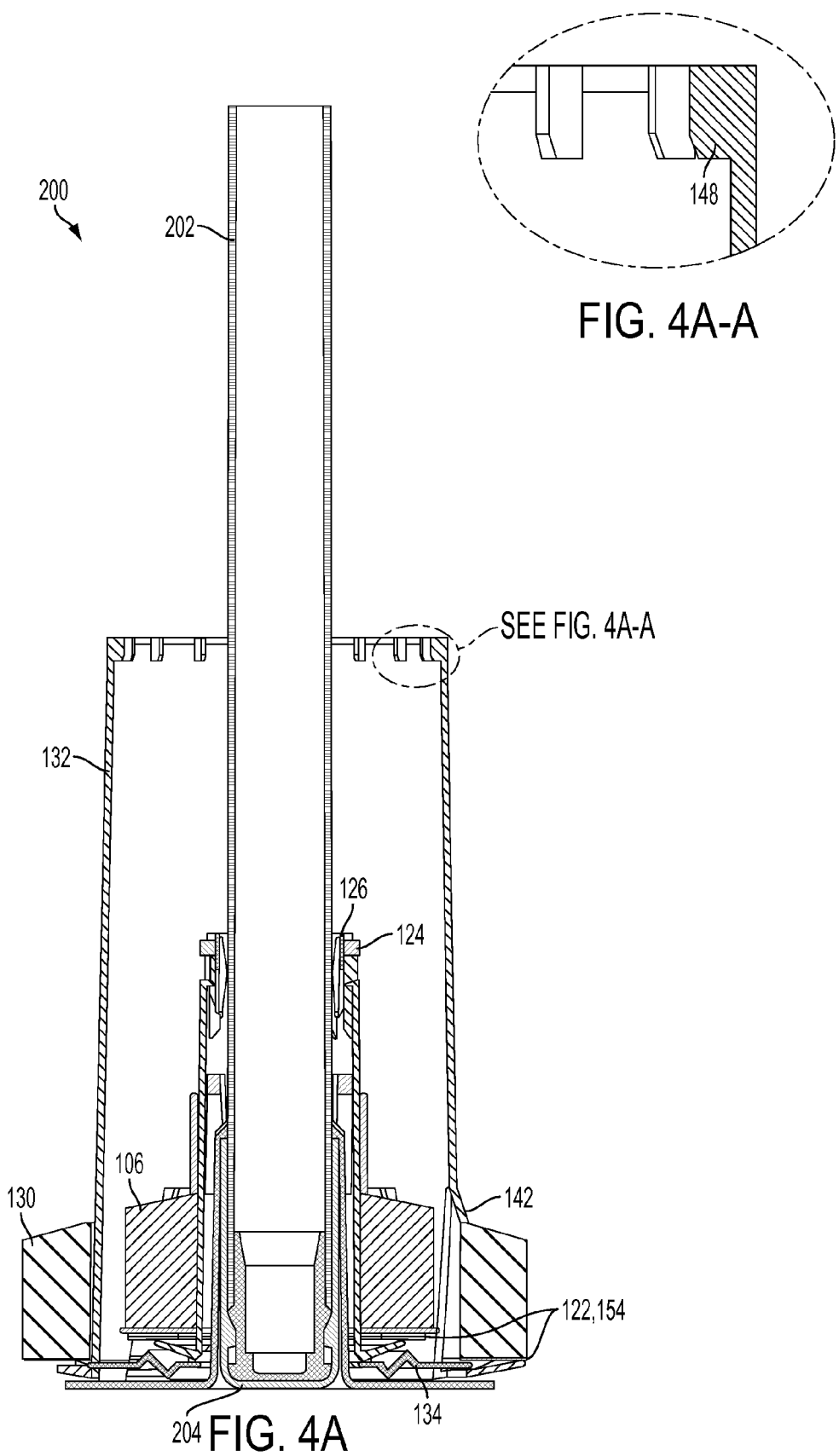

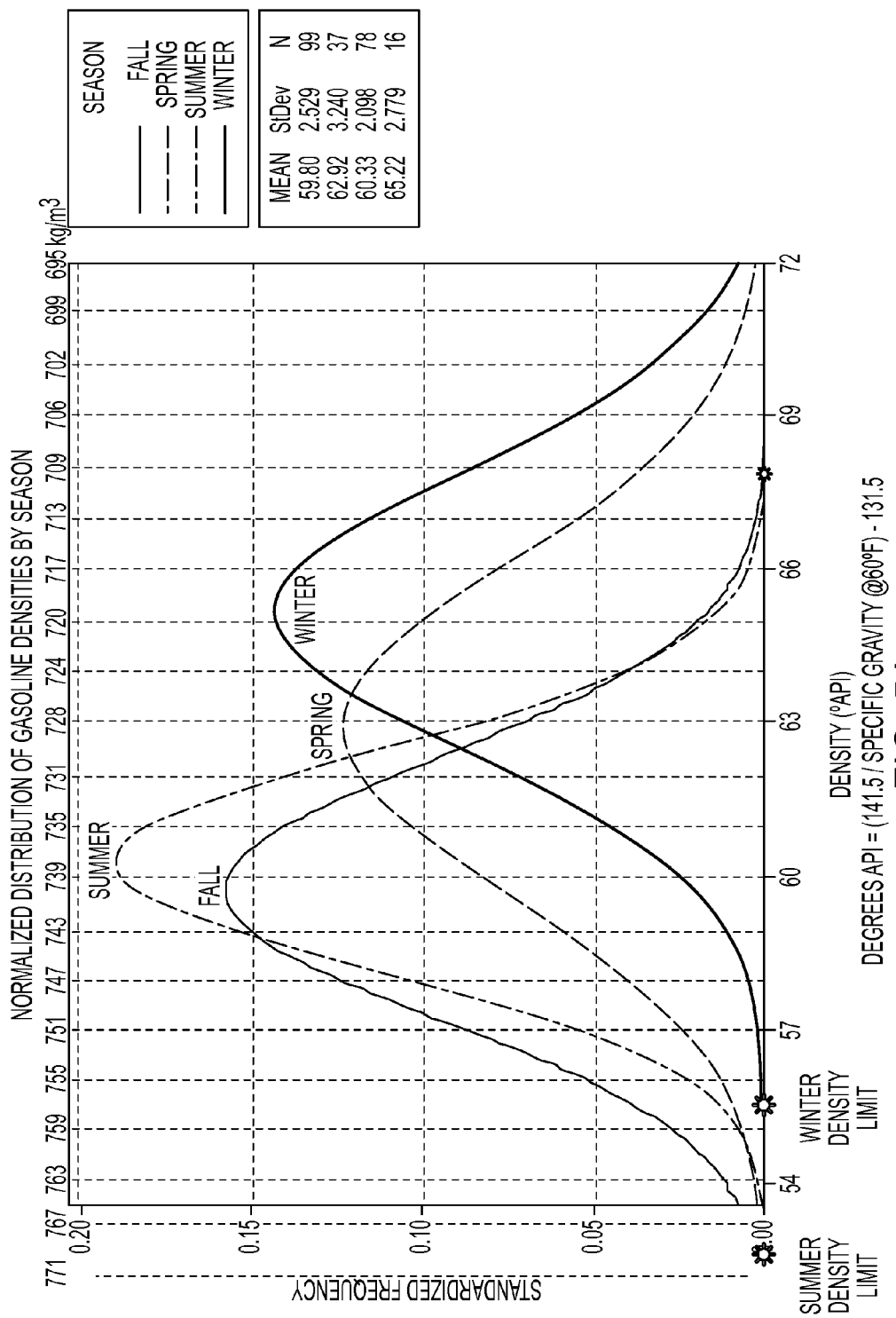

MAGNETOSTRICTIVE PROBE HAVING PHASE SEPARATION FLOAT ASSEMBLY

PRIORITY CLAIM

This application claims the benefit of provisional application Ser. No. 61/367,677, filed Jul. 26, 2010, to which priority is claimed and which is relied upon and incorporated herein by reference.

FIELD OF THE INVENTION

The present invention relates generally to devices for monitoring liquid fuel in storage tanks. More specifically, the present invention relates to a magnetostrictive probe for monitoring liquid fuel in a storage tank which is operative to determine whether phase separation has occurred.

BACKGROUND OF THE INVENTION

Fueling environments normally have fuel storage tanks, typically located underground, from which liquid fuel (e.g., gasoline or diesel fuel) is pumped to dispensers. To comply with environmental laws, rules, and regulations, these storage tanks may be double-walled and associated with various inventory reconciliation systems. Typically, these inventory reconciliation systems comprise a magnetostrictive probe which extends into the tank and comprises one or more floats adapted to move vertically therealong. The floats have magnets which, in conjunction with a tank monitor or other suitable control system, facilitate determination of the level (and thus amount) of the product stored in the tank. In particular, a magnetostrictive probe usually comprises a fuel level float that is designed to float on the interface between fuel and vapor in the storage tank ullage. One example of a magnetostrictive probe may be the Mag Plus™ Leak Detection Probe, sold by Veeder-Root Company of 125 Powder Forest Drive, Simsbury, Conn. 06070, the assignee of the present application.

Additionally, water may enter fuel storage tanks in various circumstances. Because water is denser than liquid fuel, it typically resides in a layer at the bottom of the storage tank. Thus, magnetostrictive probes usually include a water level float to determine the level of water in the storage tank. Because of the distinct difference in densities between water and liquid fuel, water level floats are designed to float on the fuel-water interface.

The measurements from these floats are reported to the tank monitor so that the operator of the fueling environment may evaluate and reconcile fuel inventory and/or detect leaks, as is well understood. One example of a tank monitor may be the TLS 450 or the TLS-350R Monitoring Systems, also sold by Veeder-Root Company. Further information on the operation of magnetostrictive probes in fueling environments is provided in U.S. Pat. No. 7,454,969, entitled "Fuel Density Measuring Device, System, and Method Using Magnetostrictive Probe Buoyancy," incorporated by reference herein in its entirety for all purposes.

However, modern fueling environments may store liquid fuels which are mixtures of gasoline and ethanol in various ratios, rather than "pure" gasoline. For example, E10 is a liquid fuel comprising 90% gasoline and 10% ethanol. Generally, it is known that gasoline containing ethanol will separate into an upper layer of gasoline and a lower layer of aqueous ethanol (also known as "phase separation") if the water concentration in the fuel becomes too great. It is desirable to know when this "phase separation" occurs so that pumping of fuel from the storage tank can be suspended until corrective action is taken.

More specifically, as small amounts of water enter the storage tank containing a gasoline/ethanol mixture, the ethanol absorbs the water. As the amount of water increases, the ternary mixture becomes unstable and most of the ethanol and water precipitate out from the gasoline to form a phase separation layer below a layer of gasoline and some ethanol. The phase separation layer has a lower density than pure water but a slightly higher density than gasoline. Further, this phase separation layer will increase in density as the amount of water added to the tank increases. For example, a "low density" phase separation layer may have a density approximately equal to 780-805 kg/m$^3$, a "medium density" layer may have a density approximately equal to 805-820 kg/m$^3$, and a "high density" layer may have a density approximately equal to 820-920 kg/m$^3$.

Traditional water level floats do not reliably detect phase separation. In particular, as noted above, water level floats are designed to float on the interface between water and gasoline. However, the aqueous ethanol layer caused by phase separation has a lower density than water, and thus the water level float may not be buoyant enough to float on this phase separation interface. Therefore, the inventory reconciliation system may not detect phase separation, and an unsuitable fuel or a phase separation mixture may be pumped to a dispenser and/or a customer's vehicle.

Moreover, design of a float that will float at the phase separation interface is problematic because many factors may affect the density of gasoline, including temperature and Reid vapor pressure. For example, where high density fuel from a cold refueling truck is added to the storage tank, the density of the fuel may be very close to that of a phase separation layer. In this case, a float designed to rise in the presence of low density phase separation may continue to rise past the phase separation interface through the high density fuel. Additionally, it is possible for a change in temperature alone to induce phase separation.

SUMMARY

The present invention recognizes and addresses disadvantages of prior art constructions and methods. According to one embodiment, the present invention comprises a phase separation float assembly for use with a fuel level probe having a shaft extending into a fuel storage tank. The phase separation float assembly comprises a first float subassembly comprising a first float adapted for vertical travel along the fuel level probe shaft and a first magnet. The first float has a first density. The phase separation float assembly also comprises a second float subassembly comprising a second float adapted for vertical travel along the fuel level probe shaft and at least one stop feature which engages the first float subassembly when the first float subassembly travels vertically a predetermined distance along the fuel level probe shaft. The second float has a second density greater than the first density. The first and second densities are selected such that, in the presence of either higher density phase separation or water, both of the first and second float subassemblies travel vertically along the shaft, and, in the presence of either a higher density fuel or lower density phase separation, only the first float subassembly travels vertically along the shaft.

According to a further embodiment, the present invention comprises a phase separation float assembly for use with a fuel level probe having a shaft extending into a fuel storage tank. The phase separation float assembly comprises a first float subassembly comprising a first float adapted for vertical travel along the fuel level probe shaft and a magnet. The first float has a first density. The phase separation float assembly also comprises a second float subassembly comprising a second float adapted for vertical travel along the fuel level probe shaft. The second float has a second density greater than the first density. The second float subassembly further comprises at least one stop feature which engages the first float subassembly when the first float subassembly travels vertically a predetermined distance along the fuel level probe shaft. The first float density is selected such that the first float subassembly travels vertically along the shaft to engage the at least one stop feature in the presence of phase separation.

According to a further embodiment, the present invention comprises a method for detecting phase separation in a fuel storage tank. The method comprises the step of providing a first float subassembly comprising a first float adapted for vertical travel along a shaft of a fuel level probe and a magnet. The method also comprises the step of providing a second float subassembly comprising a second float adapted for vertical travel along the fuel level probe shaft and at least one stop feature which engages the first float subassembly when the first float subassembly travels vertically a predetermined distance along the fuel level probe shaft. Further, the method comprises evaluating the position of the first float subassembly along the fuel level probe shaft using the magnet and determining whether the first float subassembly has traveled a distance greater than the predetermined distance.

In a further embodiment, the present invention comprises a fuel level probe for measuring the height of one or more fluids in a fuel storage tank. The fuel level probe comprises a shaft extending into the fuel storage tank, and the shaft comprises a ferromagnetic wire. The probe further comprises control electronics in electrical communication with the ferromagnetic wire to generate an interrogation pulse along the ferromagnetic wire. Also the probe comprises a first float subassembly comprising a first float adapted for vertical travel along the fuel level probe shaft. The first float has a first density, and the first float subassembly further comprises a magnet which causes a torsional wave in the ferromagnetic wire in response to the interrogation pulse. The probe also comprises a second float subassembly comprising a second float adapted for vertical travel along the fuel level probe shaft. The second float has a second density greater than the first density. The second float subassembly further comprises at least one stop feature which engages the first float subassembly when the first float subassembly travels vertically a predetermined distance along the fuel level probe shaft. The first float density is selected such that the first float subassembly travels vertically along the shaft to engage the at least one stop feature in the presence of phase separation.

According to a further embodiment, the present invention comprises a phase separation detection system for detecting phase separation in a fuel storage tank. The phase separation detection system comprises a fuel level probe comprising a shaft extending into the fuel storage tank and a control system in electronic communication with the fuel level probe. The system also comprises a first float subassembly comprising a first float adapted for vertical travel along the fuel level probe shaft and a first magnet and a second float subassembly comprising a second float adapted for vertical travel along the fuel level probe shaft. The second float subassembly further comprises at least one stop feature which engages the first float subassembly when the first float subassembly travels vertically a predetermined distance along the fuel level probe shaft. The respective densities of the first and second floats are selected such that, in the presence of phase separation, the first float subassembly travels vertically along the shaft to engage the at least one stop feature.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one of ordinary skill in the art, is set forth in the specification, which makes reference to the appended drawings, in which:

FIGS. 4A-4B are cross-sectional views illustrating the operation of a phase separation float assembly in the presence of low density phase separation or high density fuel according to one embodiment of the present invention.

FIG. 5A is an exemplary graph illustrating a normal distribution of gasoline density by season which may be used by a tank monitor to determine whether phase separation has occurred according to one embodiment of the present invention.

Figure 1:
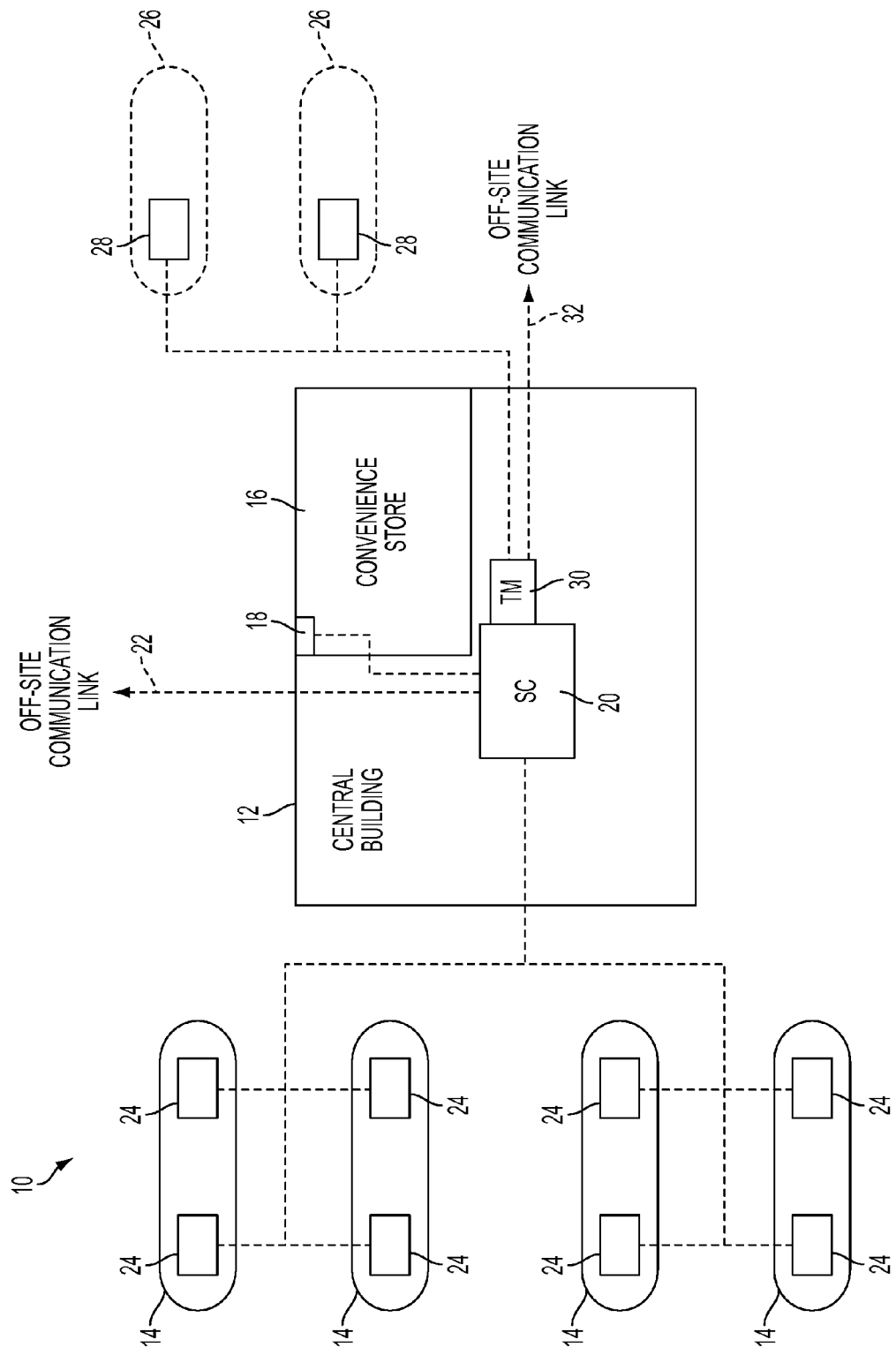
FIG. 1 is a schematic illustration of an exemplary fueling environment in which a phase separation float assembly of the present invention may be used.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

In general, the present invention relates to a magnetostrictive probe used in a storage tank for liquid fuel, including "pure" gasoline and gasoline-ethanol blends. (As those of skill in the art are aware, pure gasoline as used herein may typically include one or more additives; for example, methyl tertiary-butyl ether (MTBE) is a common additive used for raising the oxygen content of gasoline.) Embodiments of this invention provide a phase separation float assembly for use at the bottom of the magnetostrictive probe to determine whether phase separation has formed in the storage tank. (As used herein, the terms "aqueous ethanol" and "phase separation" are used interchangeably.) In one embodiment, the float assembly comprises two float subassemblies having floats of different densities. Both of the float subassemblies are adapted to move vertically along the magnetostrictive probe located in the fuel tank.

In a further embodiment, a first float subassembly (e.g., an inner float subassembly) is provided with a magnet which can be detected to determine the location of the first float subassembly along the probe shaft. The second float subassembly (e.g., an outer float subassembly), in contrast, is not provided with a magnet in this embodiment. However, the second float subassembly is less buoyant than the first float subassembly such that there are some situations in which the first float subassembly and not the second float subassembly will rise. The overall device is configured such that, if the two float subassemblies are not rising together, the first float subassembly will eventually engage a stop feature attached to the second float subassembly such that further upper movement of the first float subassembly is prevented.

In preferred embodiments, the device is constructed such that the first float subassembly will rise in the presence of both high density fuel or phase separation. However, the second float subassembly will rise only in the presence of water or high density phase separation. Thus, the presence of phase separation or water may be indicated if both float subassemblies rise, depending on the type of fuel in the storage tank. If only the first float subassembly rises, a control system is provided to interpret whether the event shows merely the presence of very dense fuel or is the result of water or phase separation. As a result, the device provides an effective arrangement for determining the presence or absence of phase separation. In accordance with a second embodiment, an additional magnet may be added to the second float subassembly, therefore allowing the probe to monitor the height of the second float subassembly to determine fluid density.

FIG. 1 provides a schematic illustration of an exemplary fueling environment 10 in which embodiments of the present invention may be used. Fueling environment 10 comprises a central building 12 and a plurality of fueling islands 14. The central building 12 may comprise a convenience store 16 having a point-of-sale (POS) 18. Further, the central building 12 may house a site controller 20, which in an exemplary embodiment may be the PASSPORT® POS system sold by Gilbarco Inc. of Greensboro, N.C., although third party site controllers may be used. Site controller 20 may control the authorization of fueling transactions and other conventional activities as is well understood, and may be incorporated into a POS, if needed or desired. Site controller 20 may be associated with an off-site communication link 22 allowing communication with a remote location for credit/debit card authorization, content provision, reporting purposes, or the like. Communication link 22 may be routed through the Public Switched Telephone Network, the Internet, both, or the like, as needed or desired.

Fueling islands 14 may have one or more fuel dispensers 24 positioned thereon. For example, fuel dispensers 24 may be the ENCORE® dispensers sold by Gilbarco Inc. Fuel dispensers 24 are in electronic communication with site controller 20.

The fueling environment 10 comprises one or more fuel storage tanks 26 adapted to store liquid fuel therein. In a typical installation, fuel storage tanks 26 are positioned underground, and may thus be referred to as USTs. However, those of skill in the art will appreciate that the present invention is also well-adapted for use in an above-ground storage tank. In addition, a magnetostrictive probe 28, described in more detail below, is associated with each UST 26 and is in electronic communication with a tank monitor 30.

Tank monitor 30, which may be in direct or indirect electronic communication with fuel dispensers 24, is provided with the hardware, software, and memory needed to reconcile the amount of fuel dispensed with current levels of fuel within USTs 26 and perform other fuel monitoring functions, as described in more detail below. Tank monitor 30 preferably communicates with the site controller 20, and may further have an off-site communication link 32 for reporting inventory, leak detection, or the like. Communication link 32 is preferably analogous to communication link 22, and in some embodiments communication links 22, 32 may be a single communication link. Finally, as described in more detail below, tank monitor 30 may preferably employ algorithms and use data stored in its memory to determine whether phase separation has occurred.

Figure 2:
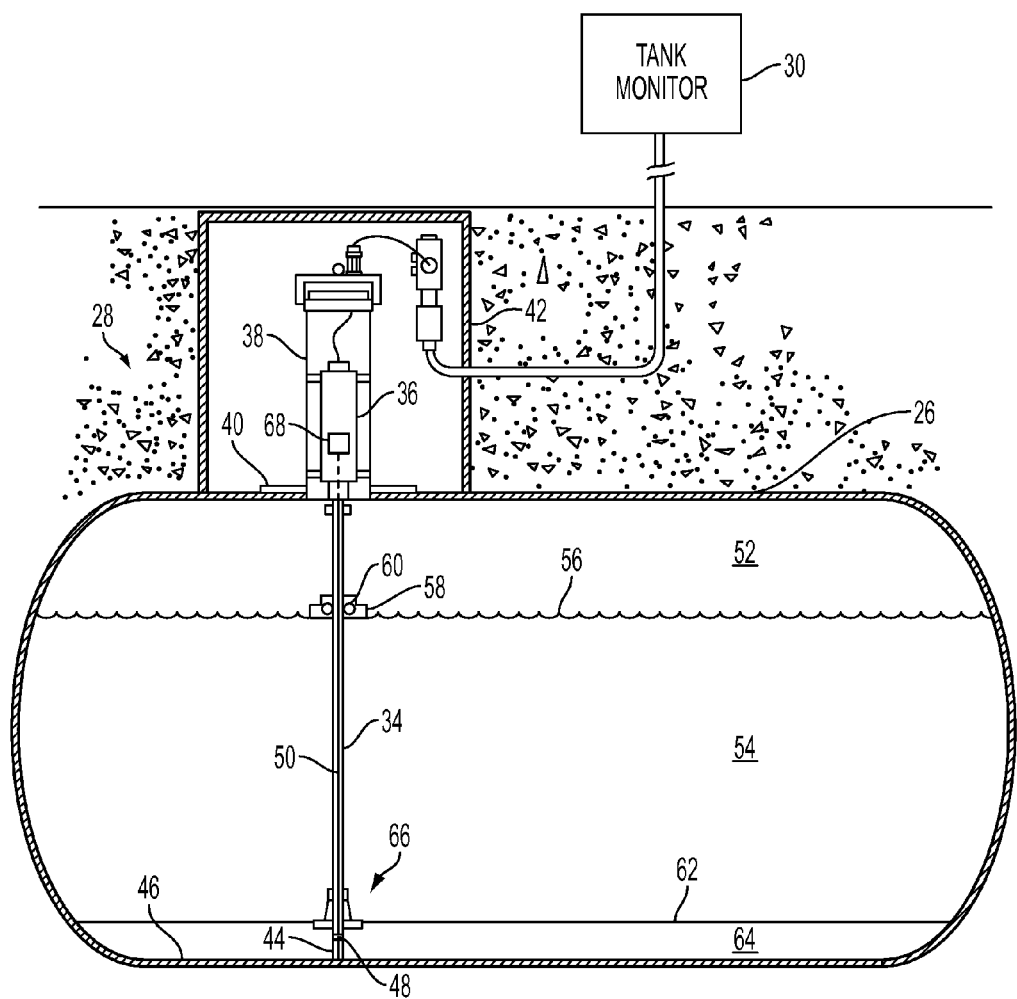
FIG. 2 is a schematic illustration of a phase separation float assembly coupled to a magnetostrictive probe in an underground storage tank according to one embodiment of the present invention.

FIG. 2 provides a schematic illustration of a phase separation float assembly coupled to magnetostrictive probe 28 in UST 26 according to one embodiment of the present invention. In particular, probe 28 includes a probe shaft 34 that extends into the UST 26. A canister 36 is positioned outside of UST 26 and is coupled to probe shaft 34. Probe 28 may be housed in a riser pipe 38, which is secured to the UST 26 via flange 40. Riser pipe 38 is preferably positioned within a sump 42, which may be double-walled.

Probe shaft 34 extends the entire depth of UST 26 through one or more fluid interfaces. In this regard, a terminal end 44 of probe shaft 34 rests on the bottom surface 46 of UST 26. Probe shaft 34 comprises a reference magnet 48 positioned proximate to the terminal end 44 of shaft 34. Reference magnet 48 may be positioned internal to the probe shaft 34, as shown, or it may be positioned externally in a boot that is situated about the terminal end 44 of probe shaft 34. A ferromagnetic waveguide or wire 50 extends coaxially along the length of probe shaft 34 to facilitate determination of the level and amount (i.e., volume or mass) of various fluids in UST 26 and/or whether phase separation has occurred. Although not specifically illustrated in FIG. 2, those of skill in the art will appreciate that one or more temperature probes or sensors are preferably associated with probe 28 and tank monitor 30 to compensate for volumetric changes in the fluids in UST 26 due to changes in temperature. In some embodiments, probe shaft 34 may comprise one or more temperature sensors.

The interface between the air and fuel vapor in ullage 52 and the fuel 54 in UST 26 defines a first fluid interface 56. An annular fuel level float 58 is positioned on the probe shaft 34. As is well understood, fuel level float 58 has a density less than the density of fuel 54 so that it will rise to float at first fluid interface 56. A fuel level permanent magnet 60 is associated with the fuel level float 58 so that the level (and amount) of the fuel in the UST 26 can be ascertained. Magnet 60 preferably has an annular configuration defining an opening therein, such that when magnet 60 is secured to float 58 on probe shaft 34, ferromagnetic wire 50 preferably extends through the opening. Fuel level float 58 is adapted to move vertically along probe shaft 34 as the level of fuel 54 in UST 26 changes. As float 58 moves along probe shaft 34, magnet 60 moves relative to ferromagnetic wire 50.

In addition, when water enters UST 26, a second fluid interface 62 in UST 26 may develop. In particular, the interface between a second fluid 64, which may be water or phase separation, and fuel 54 defines second fluid interface 62. In other words, where fuel 52 in UST 26 is "pure" gasoline, second fluid 64 (when present) is water. Likewise, where fuel 52 in UST 26 is a gasoline-ethanol blend, water entering UST 26 may cause phase separation such that second fluid 64 comprises a layer of phase separation. Those of skill in the art will appreciate that the depth of second fluid interface 62 will vary based on a number of factors, such as the amount of water entering UST 26, the temperature of fuel 54, and the ethanol content, if any, of fuel 54.

As described in more detail below, a phase separation float assembly 66 is also positioned on the probe shaft 34. Float assembly 66 comprises two float subassemblies adapted to move vertically along probe shaft 34. An inner float subassembly and an outer float subassembly are provided, wherein (in this example) the inner float subassembly has a lower density than the outer float subassembly. In one embodiment, the inner float subassembly is provided with a permanent magnet, such that when the inner float subassembly moves relative to probe shaft 34, the permanent magnet moves relative to ferromagnetic wire 50.

Phase separation float assembly 66 normally rests on or floats proximate the bottom surface 46 of UST 26. However, where water enters UST 26 and second fluid interface 62 develops, either the inner float subassembly or both float subassemblies may rise to float at second fluid interface 62. Whether both float subassemblies rise depends on the density of second fluid 64. In the embodiment illustrated in FIG. 2, both the inner float subassembly and outer float subassembly have risen to float at second fluid interface 62. This may indicate that second fluid 64 is either dense aqueous ethanol (i.e., phase separation has occurred) or water, depending on the type of liquid fuel 54 in UST 26.

Those of skill in the art understand that a magnetostrictive probe generates data regarding the level of a float in a fuel storage tank. For example, control electronics 68 are typically associated with probe 28 to control the operation thereof. Generally, control electronics 68 generates and sends an interrogation pulse along ferromagnetic wire 50. The interrogation pulse is transmitted down wire 50, creating an electromagnetic field along the length of wire 50. The magnetic fields of the permanent magnets in fuel level float 58 and phase separation float assembly 66 interact with the magnetic field generated by the interrogation pulse, causing a torsional wave in wire 50. This torsional wave travels along wire 50 and encounters a transducer in control electronics 68 (e.g., a pickup coil) capable of detecting the torsional wave. Control electronics 68 measures the time elapsed between the interrogation pulse and the arrival of torsional waves from each magnet.

Control electronics 68 are in electronic communication with tank monitor 30 and communicate measured data signals generated in the operation of probe 28 to tank monitor 30 for further processing. For example, because the speed of the torsional wave in wire 50 is known, it is possible to calculate the distance between the magnet that induced the torsional wave and the transducer or the reference magnet 48. Thus, the positions of float 58 and float assembly 66 along probe shaft 34 may be determined. In addition, tank monitor 30 may determine the amount of one or more fluids in UST 26 and/or whether phase separation has occurred. In one embodiment, control electronics 68 are housed in canister 36. However, in alternative embodiments, tank monitor 30 may comprise some or all of the components of control electronics 68.

Figure 3A:
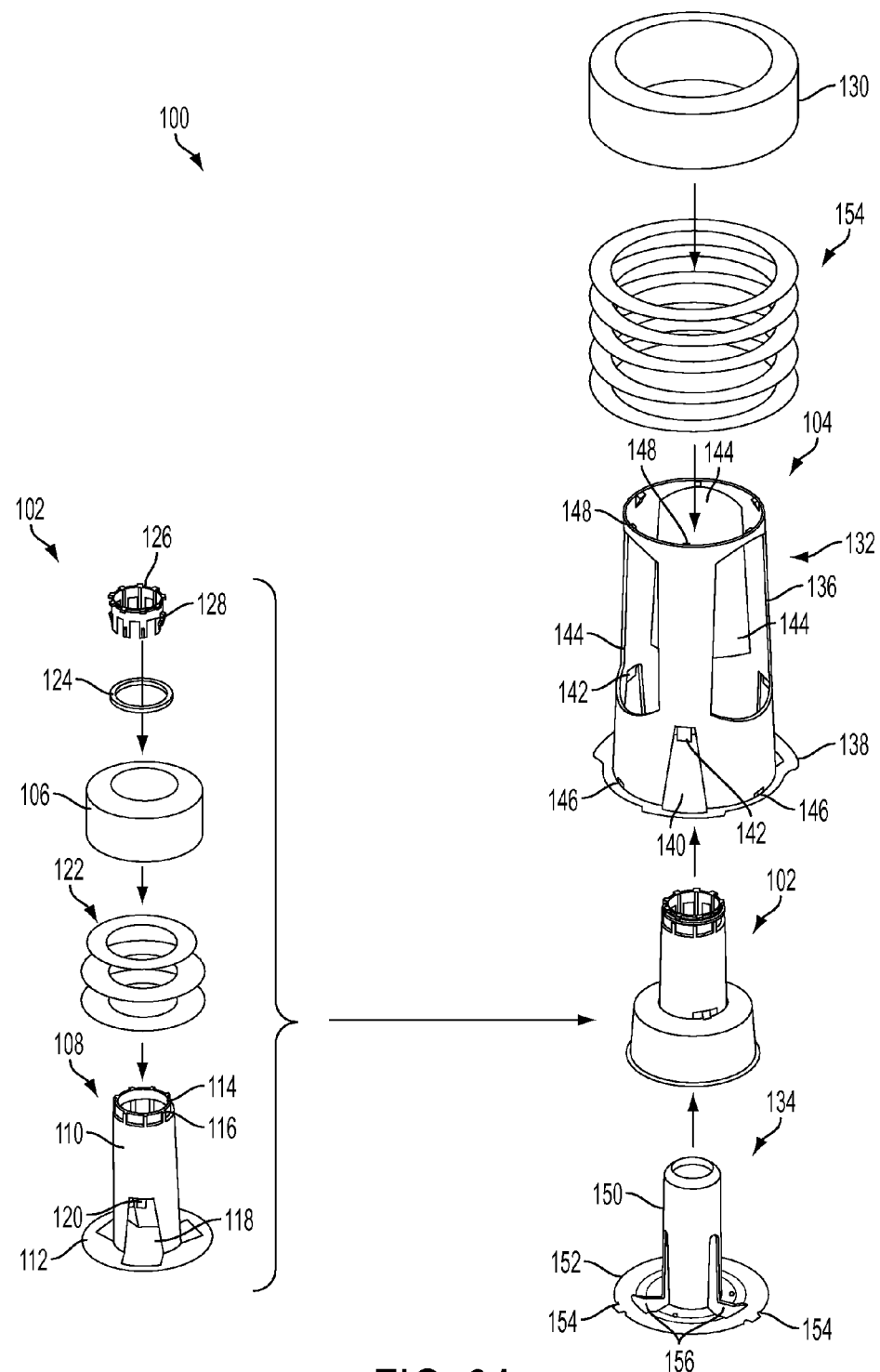
FIG. 3A is an exploded perspective view of a phase separation float assembly according to one embodiment of the present invention.
Figure 3B:
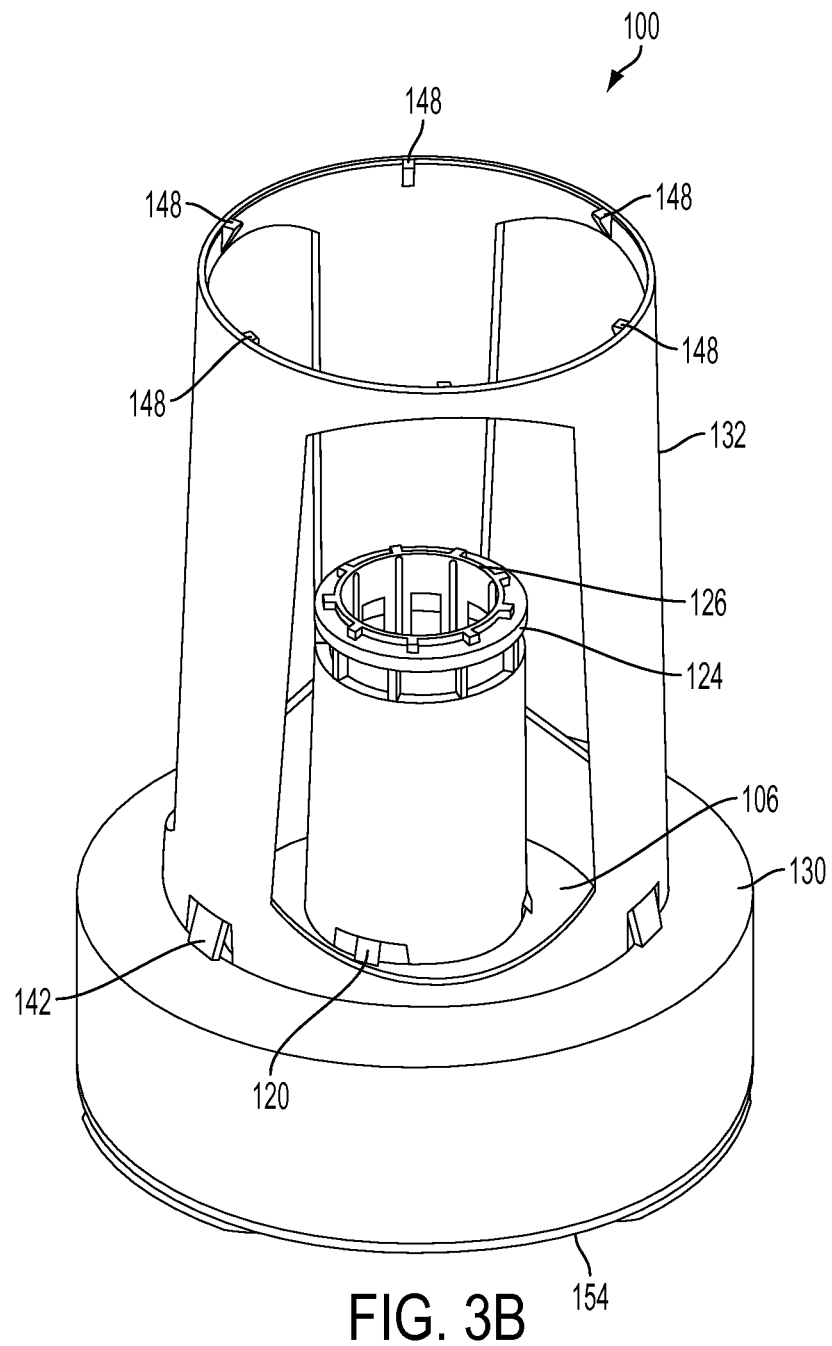
FIG. 3B is a perspective view of the phase separation float assembly of FIG. 3A in assembled condition.

The construction of the phase separation float assembly according to one embodiment of the present invention will now be described with reference to FIG. 3A, which provides an exploded perspective view of a phase separation float assembly 100, and FIG. 3B which provides a perspective view of the phase separation float assembly 100 of FIG. 3A when assembled. Generally, phase separation float assembly 100 comprises two subassemblies: an inner float subassembly 102 and an outer float subassembly 104.

First, inner float subassembly 102 comprises an inner float 106 and an inner float housing 108. Inner float 106 is configured as an annular structure defining an opening therethrough. Preferably, inner float 106 is formed from a material such as foam or NITROPHYL®. Further, the density of inner float 106 is preferably selected such that the density of subassembly 102 is lower than the respective densities of water and low density phase separation over the range of operating temperatures of float assembly 100. Further, it is preferred that the density of inner float subassembly 102 be slightly less than the density of dense liquid fuel. In a preferred embodiment, inner float subassembly 102 may have a density approximately equal to 790 kg/m$^3$ so that it will rise along the shaft of a magnetostrictive probe in the presence of any one of the above liquids. See also FIG. 5b.

In the illustrated embodiment, inner float housing 108 may comprise a hollow, generally cylindrical body portion 110 and a substantially flat base portion 112. Body portion 110, in this example, first defines a stepped top edge 114 having a diameter slightly smaller than that of body portion 110 and surrounded by a plurality of circumferentially-spaced rails 116. Body portion 110 further defines a plurality of circumferentially-spaced apertures 118 which extend from base portion 112 upwards a distance slightly greater than the height of inner float 106. The peripheral edges of each aperture 118 define a semirigid tab 120 which depends from and extends outward at an angle from body portion 110. Base portion 112 has a diameter slightly greater than the outer diameter of inner float 106 and extends perpendicularly from the bottom edge of body portion 110. The inner diameter of inner float 106 may preferably be just large enough to be snugly received over the body portion 110 of inner float housing 108. Inner float housing 108 may be formed of a variety of materials suitable for operation in the presence of petroleum products.

One or more substantially flat, annular ballasts 122 are received over body portion 110 intermediate base portion 112 and inner float 106. Those of skill in the art will appreciate that ballasts 122 provide stability to and may be used to adjust the buoyancy of inner float subassembly 102 in operation. It will be appreciated that as inner float 106 slides downwards along body portion 110, tabs 120 will bend inward into apertures 118 until further movement of inner float 106 is prevented by base portion 112. Then, tabs 120 again extend outward from body portion 110 to retain inner float 106 on inner float housing 108. Thus, housing 108 will rise along with float 106.

Additionally, in a preferred embodiment, an annular permanent magnet 124 is coupled to inner float subassembly 102. For example, in one embodiment, magnet 124 may be received over rails 116 of body portion 110. A collar 126 may define a plurality of flexible snap fasteners 128 with a diameter equal to the inner diameter of body portion 110. To retain magnet 124 on rails 116, fasteners 128 of collar 126 may snap into place below stepped top edge 114 in body portion 110 and a plurality of tabs on the top edge of collar 126 may prevent vertical movement of magnet 124. Those of skill in the art will appreciate that other suitable means of coupling magnet 124 to subassembly 102 may be used.

As noted above, in some preferred embodiments of the phase separation float assembly of the present invention, only one magnet is provided. Those of skill in the art will appreciate that this is advantageous because the float assembly may be easily used as a retrofit with many existing magnetostrictive probes already installed in the field. Specifically, the magnetostrictive probe on which the phase separation float assembly is received does not need to be reprogrammed. Any programming changes that may be required by replacing a traditional water level float with the phase separation float assembly need be made only at the tank monitor. Programming changes to the tank monitor may be easily made and also be made remotely (e.g., using off-site communication link 32).

Next, outer float subassembly 104 comprises an outer float 130, an outer float housing 132, and a retainer 134. Outer float 130 is configured as an annular structure having an opening therethrough that is in many ways similar to inner float 106. However, outer float 130 has a larger outer diameter than inner float 106. The inner diameter of outer float 130 is preferably just large enough to snugly be received over outer float housing 132. Thus, outer float 130 circumferentially surrounds inner float 106 when phase separation float assembly 100 is fully assembled.

Outer float 130 has a higher density than inner float 106 in this embodiment. More specifically, the density of outer float 130 is preferably selected such that the density of outer float subassembly 104 is lower than the respective densities of high density phase separation and water, but higher than the density of liquid fuel. Further, to prevent the possibility of both float subassemblies in phase separation float assembly 100 rising in the presence high density fuel, the density of which can be very close low density phase separation (i.e., to prevent "false positive" indications of phase separation), it is also preferred that the density of outer float subassembly 104 be greater than that of low density phase separation for the majority of temperatures in the range of operation of phase separation float assembly 100. In a preferred embodiment, outer float subassembly 104 may have a density approximately equal to 820 kg/m$^3$ so that it will typically rise along the shaft of a magnetostrictive probe in the presence of water or high density phase separation. See also FIG. 5b.

Outer float housing 132 is in some respects similar to inner float housing 108. Thus, outer float housing 132 is preferably formed having a generally cylindrical hollow body portion 136 and a substantially flat base portion 138 extending perpendicularly from the bottom edge of body portion 136. In addition, body portion 136 defines a plurality of circumferentially-spaced apertures 140 about its base. Further, the upper periphery of each aperture 140 define a semirigid tab 142 which depends from and extends out at an angle from body portion 136.

However, outer float housing 132 also preferably defines one or more windows 144. Those of skill in the art will appreciate that windows 144 may facilitate fuel flow around floats 106, 130 and allow easy movement of each float subassembly 102, 104 along the shaft of a magnetostrictive probe. In the illustrated embodiment, three circumferentially-spaced windows 144 are provided. Windows 144 are generally rectangular in shape and begin a distance from base portion 138 slightly greater than the height of outer float 130 and extend to just below the top edge of body portion 136. Finally, outer float housing 132 may define a series of slots 146 to facilitate attachment of retainer 134.

Additionally, outer float housing 132 preferably defines a stop feature circumferentially along the upper edge of body portion 136. The stop feature may comprise, for example, a lip or a plurality of teeth. In any case, the stop feature is designed to limit the inner float subassembly 102's vertical travel beyond the upper edge of outer float housing 132. In the illustrated embodiment, for example, body portion 136 defines six circumferentially-arranged teeth 148 having an inner diameter smaller than the outer diameter of base portion 112 of inner float housing 108. Thus, where the inner float subassembly 102 rises in the presence of low density phase separation or high density fuel, the outer float subassembly 104 will not rise and base portion 112 of the inner float subassembly will eventually engage teeth 148 on body portion 136. As explained in more detail below, a tank monitor or other suitable control system may use algorithms and other information to interpret this event and determine whether phase separation has occurred.

Retainer 134 defines the lower extent of inner float subassembly 102's travel along the magnetostrictive probe shaft. In the illustrated embodiment, retainer 134 comprises a generally cylindrical hollow shaft 150 designed to receive inner float subassembly 102 slidably thereon and a perpendicularly-extending base portion 152. During assembly, retainer 134 may be attached to outer float housing 132 to assemble inner float subassembly 102 with outer float subassembly 104. For example, base portion 152 may define a series of tabs 154 which are received in slots 146 in outer float housing 132. In some embodiments, retainer 134 may also define a series of circumferentially-spaced slots 156 to facilitate fluid flow therethrough.

In much the same way as inner float 106 is attached to inner float housing 108, outer float 130 is received over body portion 136 of outer float housing 132. One or more substantially flat, annular ballasts 154 may be positioned intermediate base portion 138 of outer float housing 132 and outer float 130. As with inner float 106, after outer float 130 is received on body portion 136, tabs 142 return outward from body portion 136 to retain outer float 130 on outer float housing 132. Thus, housing 132 will rise along with float 130. Further, where outer float subassembly 104 rises in the presence of a fluid more dense than outer float subassembly 104, it will be appreciated that inner float subassembly 102 will also rise.

Figure 4B:
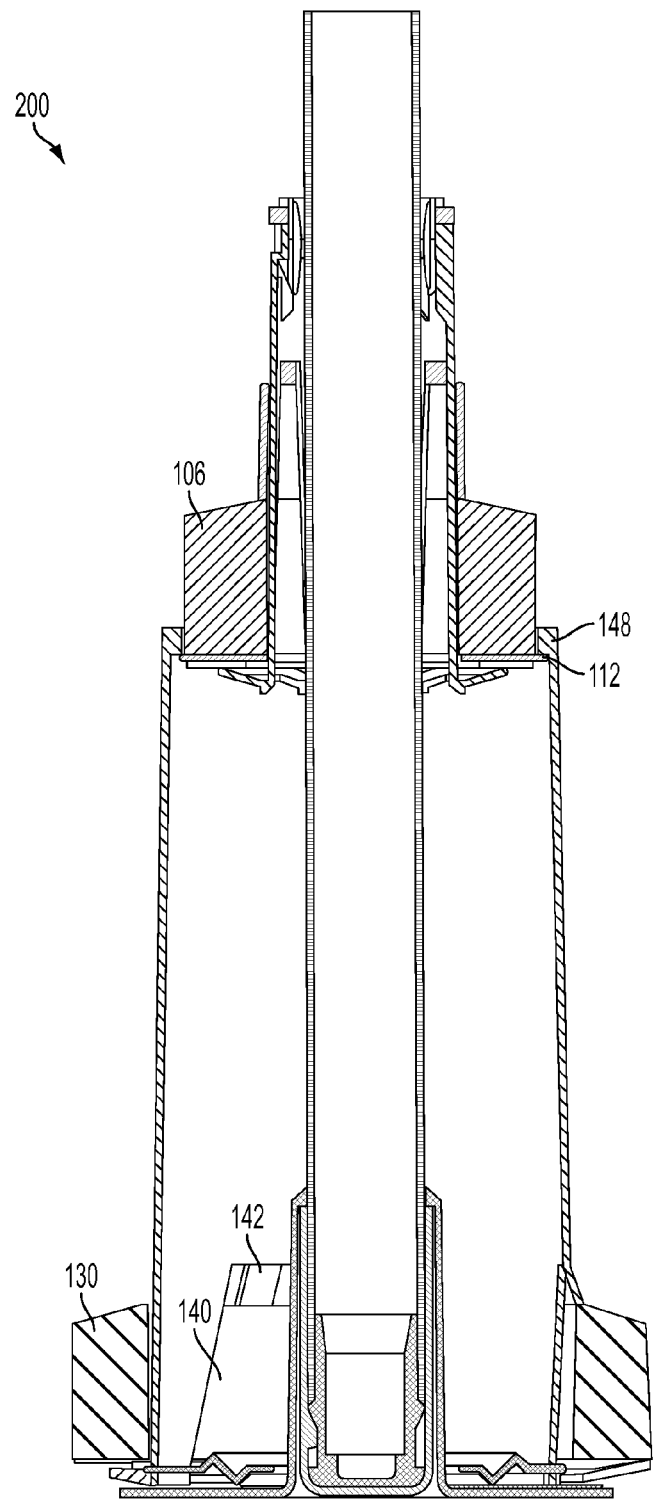

The operation of a phase separation float assembly in accordance with aspects of the present invention may be described with reference to FIGS. 4A-6. First, FIGS. 4A-4B provide cross-sectional views illustrating the operation of a phase separation float assembly 200 in the presence of low density phase separation or high density fuel according to one embodiment of the present invention. Phase separation float assembly 200 is analogous to phase separation float assembly 100, and like reference numerals are used to refer to like features. FIG. 4A illustrates phase separation float assembly 200 received over a shaft 202 of a magnetostrictive probe in the presence of liquid fuel in a storage tank. Shaft 202 is provided with a boot 204, which preferably houses a reference magnet as described above. Here, because the respective densities of inner float subassembly 102 and outer float subassembly 104 are greater than that of liquid fuel, both floats rest at the bottom of the storage tank. As explained above, the magnetostrictive probe provides data regarding the position of magnet 124 in inner float subassembly 102 to a tank monitor, such as tank monitor 30, for further processing. Further, one or more temperature probes are also preferably associated with the storage tank or the magnetostrictive probe to communicate to the tank monitor data regarding the temperature of the fluid in the storage tank.

Depending on the density of the fluid surrounding floats 106, 130, either inner float subassembly 102 or both float subassemblies 102, 104 may rise. The magnetostrictive probe will communicate data regarding the changing position of the magnet 124 in inner float subassembly 102 to tank monitor 30. Then, tank monitor 30 may use this information to determine whether phase separation has occurred and/or the level and amount of water or aqueous ethanol in the storage tank. For example, if both subassemblies 102, 104 rise such that magnet 124 travels vertically above the limit otherwise imposed by the stop feature (i.e., teeth 148 in this example) on housing 132, this indicates that the fluid surrounding the phase separation float assembly 200 has a density greater than the combined density of inner float subassembly 102 and outer float subassembly 104. Thus, tank monitor 30 may interpret this event as phase separation or water entering the storage tank.

More specifically, in many embodiments it is preferred that the combined density of both inner float subassembly 102 and outer float subassembly 104 be greater than that of high density fuel over the range of operating temperatures, such that the entire assembly will rise in low density phase separation but not high density fuel. Thus, where the inner float 106 first rises alone to engage teeth 148, and then the entire phase separation float assembly 200 rises, this will indicate that phase separation has occurred. In a preferred embodiment, the combined density of inner float subassembly 102 and outer float subassembly 104 may be approximately equal to 810 kg/m$^3$.

In contrast, FIG. 4B illustrates phase separation float assembly 200 in the presence of a fluid having a density greater than that of inner float subassembly 102 and less than that of outer float subassembly 104. Thus, the inner float subassembly 102 has risen to the point at which base portion 112 of inner float housing 108 engages teeth 148 on outer float housing 132 and stopped. As explained above, where inner float subassembly 102 rises but outer float subassembly 104 does not, either low density aqueous ethanol resulting from phase separation or high density fuel may be present.

In this case, to make a determination of whether phase separation has occurred, tank monitor 30 may employ algorithms and additional data stored in memory related to the various fluids that may be present in the storage tank. In one example, tank monitor 30 may employ data regarding temperature and density relationships for various fluids that may be present in the storage tank. In this regard, FIG. 5A is an exemplary graph illustrating a normalized distribution of gasoline density by season. Thus, FIG. 5A illustrates the probability that gasoline density will fall within the indicated ranges for each season. From this, tank monitor 30 may also store information regarding the mean, minimum, and maximum values for gasoline density during each season.

Figure 5B:
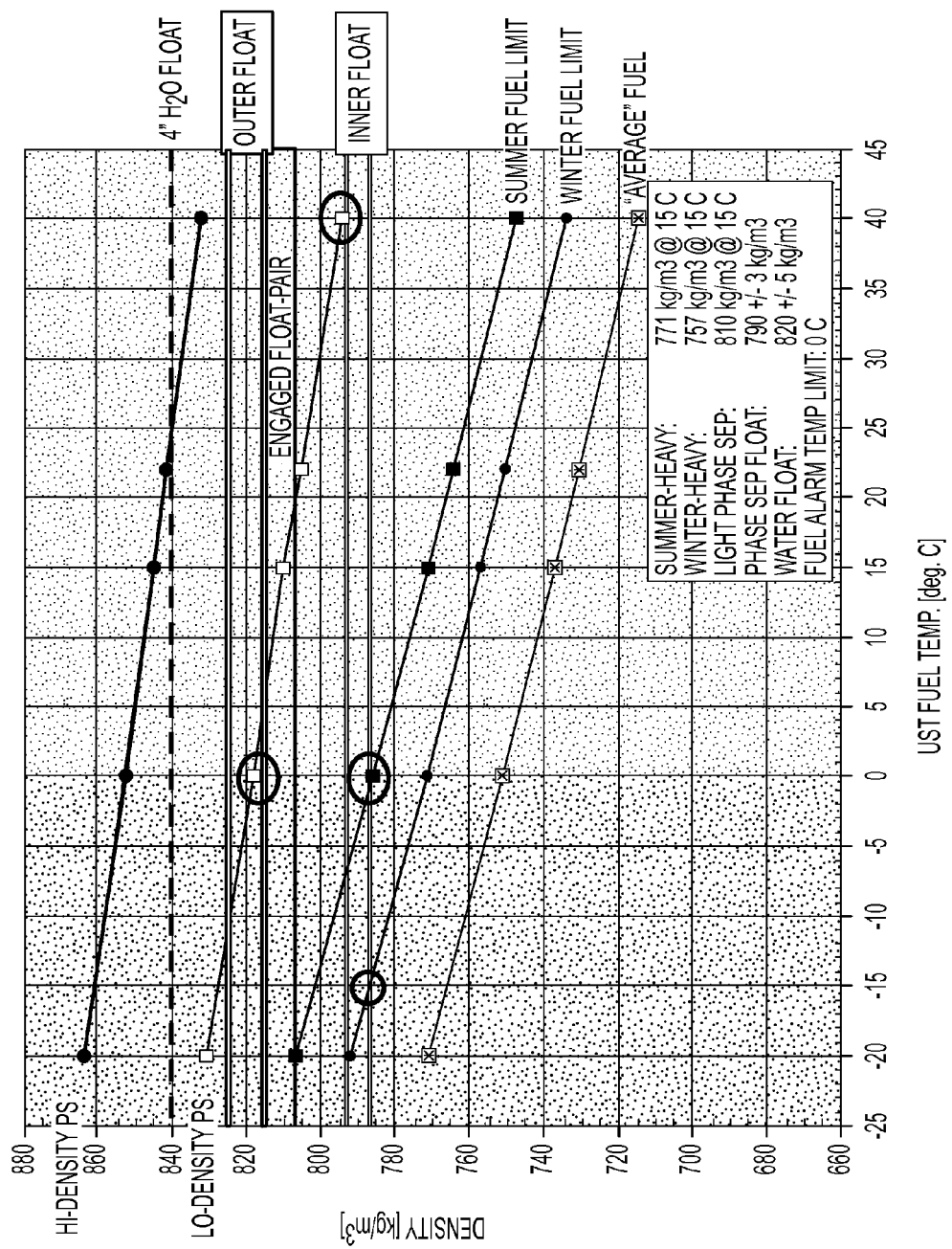
FIG. 5B is an exemplary graph illustrating the relationship between the density and temperature of various fluids in a fuel storage tank which may be used by a tank monitor to determine whether phase separation has occurred according to one embodiment of the present invention.

Further, the memory of tank monitor 30 may comprise observational data regarding the density of phase separation and the density of gasoline in each season over a range of temperatures. For example, FIG. 5B is an exemplary graph illustrating the relationship between the density and temperature of high and low density phase separation ("PS") and "average" liquid fuel. Further, FIG. 5B illustrates the relationship between the maximum density and temperature of liquid fuel in the summer and winter. Finally, this figure shows the respective densities of the inner float subassembly, outer float subassembly, and the engaged float-pair of a phase separation float assembly according to one embodiment of the present invention.

Tank monitor 30 may use the above information to predict whether the rise of inner float subassembly 102 is due to phase separation or high density fuel. For example, inner float subassembly 102 will typically rise only in the presence of a fluid with a greater density than inner float subassembly 102. Because the density of inner float subassembly 102 and the temperature of the fluid are known to tank monitor 30, tank monitor 30 may use the above information to determine the expected densities of liquid fuel and phase separation. If the density of inner float subassembly 102 is greater than the expected density of the liquid fuel for a given temperature (e.g., 15° C.), it increases confidence that the inner float is rising in the presence of phase separation.

In a further example, tank monitor 30 may determine whether high density fuel is present using data regarding the movement of magnet 124 over a period of time. First, phase separation often develops relatively slowly in a known fashion. An inner float subassembly rising as a result of phase separation may therefore change position according to a characteristic rate and/or pattern. In contrast, when high density fuel is present (such as when cold fuel is introduced into a storage tank), the inner float subassembly may rapidly rise and engage the stop feature on the outer float subassembly housing. However, the temperature of the newly-introduced fuel will increase over time (reducing the density of the fuel) and the inner float subassembly's level will decrease. Thus, tank monitor 30 may analyze the changes and rates of change in position of magnet 124 to distinguish between high density fuel and phase separation. Further, as noted above, tank monitor 30 preferably is in electronic communication with one or more fuel temperature probes. Therefore, further confidence can be gained that high density fuel is present by correlating a change in fuel temperature with a corresponding change in position of the inner float subassembly.

Figure 6:
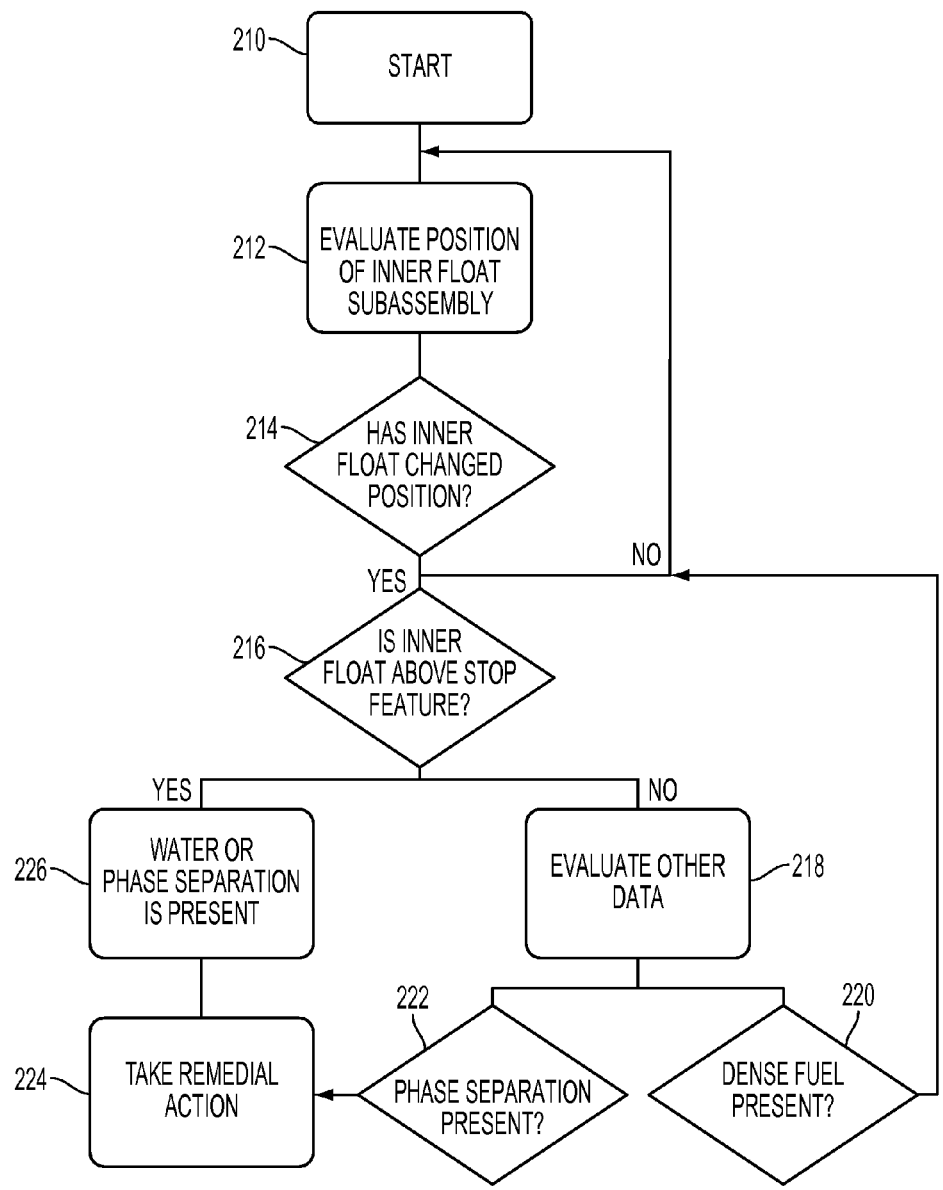
FIG. 6 is a flowchart outlining steps that may be performed by a tank monitor in evaluating the change in position of one or both floats in a phase separation float assembly according to one embodiment of the present invention.

FIG. 6 summarizes steps that may be performed by a tank monitor in evaluating the change in position of one or both float subassemblies in a phase separation float assembly in accordance with an embodiment of the present invention. The process starts (step 210) and a tank monitor receives and evaluates data signals from a magnetostrictive probe regarding the position of a magnet on the inner float subassembly of a phase separation float assembly (step 212). The tank monitor first determines whether the inner float subassembly has changed position (step 214). If not, the tank monitor continues to evaluate the position of the magnet on the inner float subassembly. If it has, the tank monitor next determines whether the magnet in the inner float subassembly has traveled vertically above the point at which it would otherwise stop if the inner float subassembly had engaged the stop feature on the outer float housing (step 216). If not, the tank monitor employs algorithms and other data to determine whether the change in position of the inner float subassembly indicates that phase separation has occurred, as described above (step 218). If the tank monitor determines that the inner float subassembly has risen due to the presence of dense fuel (step 220), it may simply continue to evaluate the position of the inner float subassembly. However, if the tank monitor determines that low density phase separation is present (step 222), then the tank monitor may take appropriate remedial action (step 224), such as stopping the pumping of liquid fuel from the storage tank. Returning to step 216, if the inner float subassembly has traveled above the stop feature in the outer float housing, this means that the outer float subassembly has risen in addition to the inner float subassembly. Here, the tank monitor may indicate the presence of water or an aqueous ethanol layer due to phase separation (step 226) and take appropriate remedial action (step 224).

Figure 7:
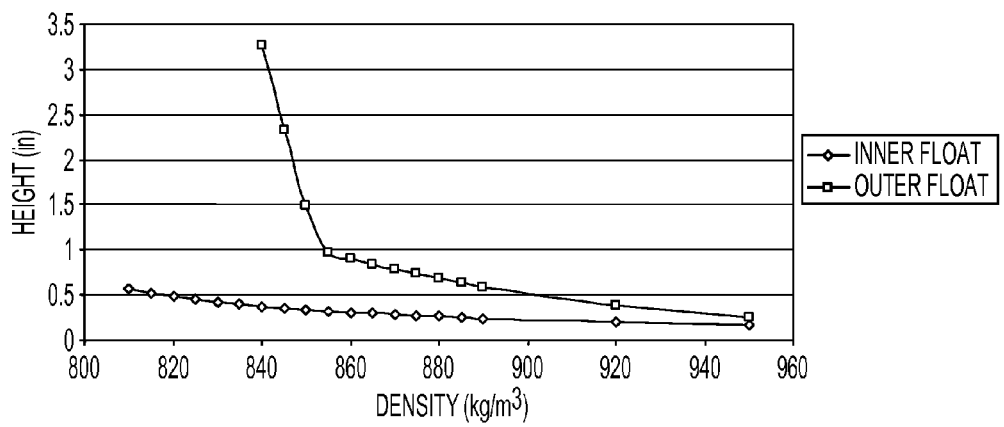
FIG. 7 is an exemplary graph illustrating the relationship between the density of a layer of fluid and the depth of the layer necessary to lift each of the inner and outer floats of a phase separation float assembly in a storage tank containing gasoline having a density of 750 kg/m$^3$ according to one embodiment of the present invention.

As noted above, the present invention may be used with liquid fuels other than gasoline-ethanol blends. Thus, in embodiments where the liquid fuel in which the phase separation float assembly resides is "pure" gasoline, the present invention maintains and improves upon the operation of a conventional water level float. For example, because the inner float subassembly is more buoyant than currently-used water level floats, the inner float subassembly may detect water at a lower level in addition to indicating the level of other liquids that are less dense than water. For example, FIG. 7 is an exemplary graph illustrating the relationship between the density of a layer of fluid and the depth of the layer necessary to lift each of the inner and outer floats of an exemplary phase separation float assembly in a storage tank containing gasoline having a density of 750 kg/m$^3$. This figure shows that as the density of the fluid layer increases (approaching the density of water), the required depth of the fluid layer necessary to cause the inner and outer floats to lift decreases. For example, where the density of the fluid layer approaches the density of water at about 950 kg/m$^3$, each of the floats will rise in about 0.25" of the fluid.

Figure 8:
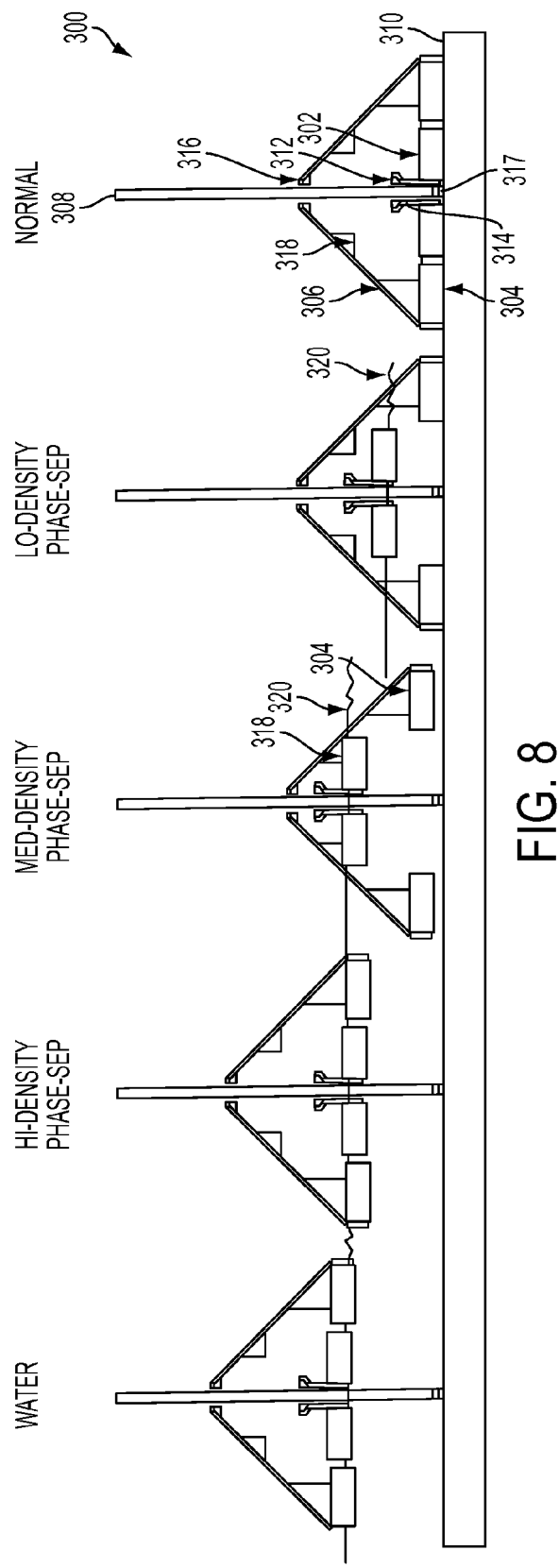
FIG. 8 is a cross-sectional view illustrating the positions of respective inner and outer floats of a phase separation float assembly in the presence of fluids of varying density according to one embodiment of the present invention.

In an alternative embodiment of the present invention, a second magnet may be attached to the outer float subassembly of a phase separation float assembly. In this regard, FIG. 8 first provides a cross-sectional view of an alternative phase separation float assembly 300. The embodiment illustrated in FIG. 8 differs from the embodiments described above in that both the inner float 302 and outer float 304 are arranged internal to a frustoconical outer float housing 306. Nevertheless, inner float 302 and outer float 304 are analogous to inner float 106 and outer float 130, respectively. Float assembly 300 is received along a magnetostrictive probe shaft 308 and may rest proximate the base 310 of a storage tank in the absence of water entering the storage tank or phase separation occurring.

In the illustrated embodiment, a first permanent magnet 312 may be coupled to the upper edge of an inner float housing 314. In addition, a second permanent magnet 316 is coupled to an upper edge of outer float housing 306. Thus, the interrogation pulse sent down the wire in the magnetostrictive probe shaft 308 generates return pulses for each magnet 312, 316 and for a reference magnet 317. The elapsed time between the return pulses may be used to determine the relative locations of each float, as described above. Further, a stop feature, which here is illustrated in the form of a square lip 318, is provided along the interior of outer float housing 306. Lip 318 is located such that its inner diameter is smaller than the outer diameter of inner float 302. Thus, when inner float 302 rises but outer float 304 does not, lip 318 will engage inner float 302 to prevent inner float 302 from further vertical translation.

Importantly, because a second magnet 316 is provided in this embodiment and associated with outer float housing 306, a tank monitor may use information regarding the relative levels of magnets 312, 316 to determine an approximate density of the fluid 320 in which the float assembly 300 resides. Specifically, the tank monitor may employ information comprising stored densities of inner float 302 and outer float 304 (or, more precisely, the densities of the subassemblies including these floats), the difference between their respective positions along probe shaft 308, the temperature of fluid 320 and of the liquid fuel, stored information regarding the density of liquid fuel at various temperatures (described above), and optionally information from a density meter, explained in more detail below. Thereby, the tank monitor may obtain an indication of the composition of a fluid layer that causes either inner float 302 or both floats 302, 304 to rise.

Figure 9:
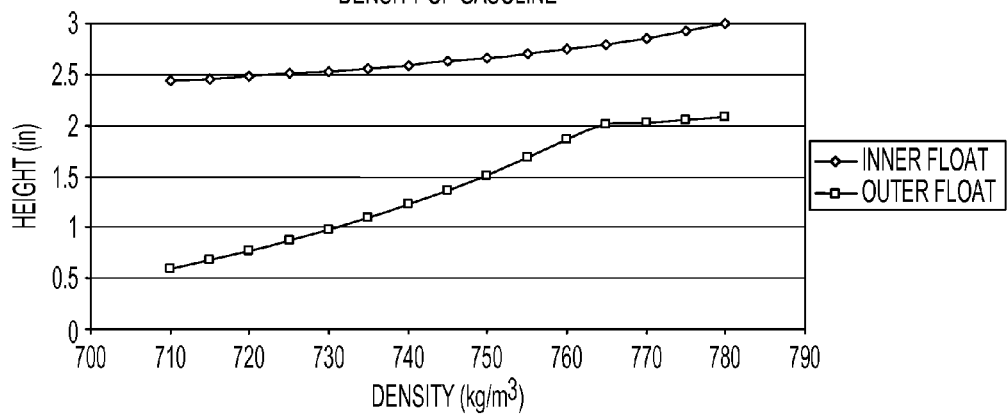
FIG. 9 is an exemplary graph illustrating the relationship between the level of each of the inner and outer floats of a phase separation float assembly in the presence of a layer of phase separation having a depth of 3" and a density of 850 kg/m$^3$ at various densities of liquid fuel according to one embodiment of the present invention.

In this regard, FIG. 9 is an exemplary graph illustrating the relationship between the level of each of the inner and outer floats of a phase separation float assembly in the presence of a layer of phase separation having a depth of 3" and a density of 850 kg/m$^3$ at various densities of liquid fuel. Data regarding the relative height of the inner and outer floats (or their respective subassemblies) in the presence of phase separation of varying depths and densities for a range of densities of liquid fuel may be stored in a memory of a tank monitor. Thus, for a given fuel density and given relative locations of inner float 302 and outer float 304, the tank monitor may calculate additional information to determine whether phase separation has occurred.

Referring again to FIG. 8, the positions of respective inner and outer floats of phase separation float assembly 300 in the presence of fluids of increasing density (when viewed from right to left) are also illustrated. For example, where phase separation float assembly 300 is in the presence of low density phase separation, inner float 302 may rise but outer float 304 will not. In the presence of phase separation having a "medium" density, inner float 302 may engage lip 318 and outer float 304 may begin to rise. Next, in the presence of phase separation having a "high" density, both inner float 302 and outer float 304 will rise to float at the phase separation interface. Finally, in the presence of water, inner float 302 and outer float 304 will rise to float at a slightly higher level on the water-fuel interface.

In some embodiments where further confidence is needed or desired, it is contemplated that the phase separation float assembly of the present invention be operated in conjunction with a density meter. In some embodiments the density meter may be coupled to the magnetostrictive probe. For example, the density meter may be analogous to the density measuring devices disclosed in commonly-owned U.S. patent application Ser. No. 12/652,607 or U.S. Pat. No. 7,454,969, both of which are incorporated herein by reference in their entirety for all purposes. In any case, those of skill in the art will appreciate that where a density meter is used to determine the density of the liquid fuel, a tank monitor may make a more accurate determination of the depth and density of a phase separation layer. Moreover, as explained above, where the density of the liquid fuel is known, the tank monitor may readily ascertain whether a rise of the inner float is due to phase separation or dense fuel.

Figure 10A:
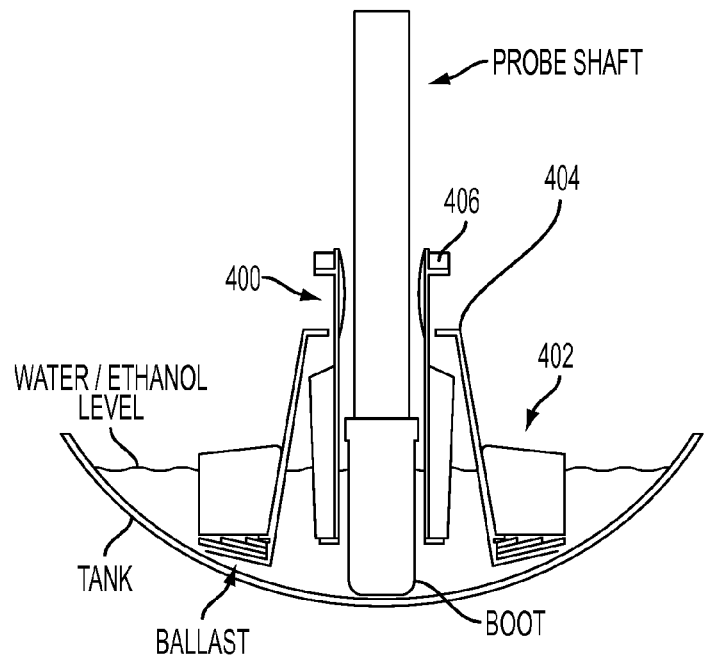
FIG. 10A is a cross-sectional view of a phase separation float assembly in a layer of phase separation in a liquid fuel storage tank according to one embodiment of the present invention.

Referring now to FIG. 10A, in a further embodiment of the present invention, a phase separation float assembly is provided with an inner float subassembly 400 and an outer float subassembly 402 having slightly different densities. As explained above, when phase separation occurs, the density of a resulting aqueous ethanol layer is lower than that of water and greater than that of gasoline. Thus, a traditional water level float may be too dense to rise in phase separation or a greater amount of phase separation is required to lift the float. In the latter case, it will be appreciated there may be a "lag" in time before the water level float rises and the tank monitor detects that phase separation has occurred.

The float assembly of the presently-described embodiment may preferably be constructed in a manner analogous to phase separation float assembly 100. However, to avoid the lag described above, the float assembly may be provided with an inner float subassembly 400 and an outer float subassembly 402 both having a density less than that of phase separation. The outer float subassembly 402 again has a density greater than that of the inner float subassembly 400, such that a greater amount of phase separation must be present to cause the outer float subassembly to rise. In other words, the inner float subassembly 400 will rise before the outer float subassembly 402 in a smaller amount of phase separation. Further, the outer float subassembly 402 housing is provided with a stop feature, here illustrated as a recessed lip 404 that restrains vertical movement of the inner float subassembly 400 as described above.

In operation, a layer of phase separation may develop that is at first sufficient to cause only the inner float subassembly 400 to rise. A tank monitor in electrical communication with the magnetostrictive probe may not record the position of the inner float subassembly 400 at this point. However, as the ethanol continues to absorb water, the density of the phase separation layer increases and the inner float subassembly 400 continues to rise, ultimately engaging the recessed lip 404 on the outer float subassembly 402. The combined density of the inner and outer float subassemblies 400, 402 is lower than that of the outer float subassembly 402 alone; consequently, the dual-float assembly will tend to rise in a smaller amount of phase separation than the outer float subassembly 402 alone. As the dual-float assembly begins to rise, a magnet 406 on inner float subassembly 400 will rise above a predetermined level. At this point, the tank monitor preferably analyzes the position of magnet 406 to determine the height of the phase separation layer, and may take remedial action, as needed. Thus, the phase separation float assembly of this embodiment may detect the presence of phase separation at a lower level than a traditional water level float could.

Figure 10B:
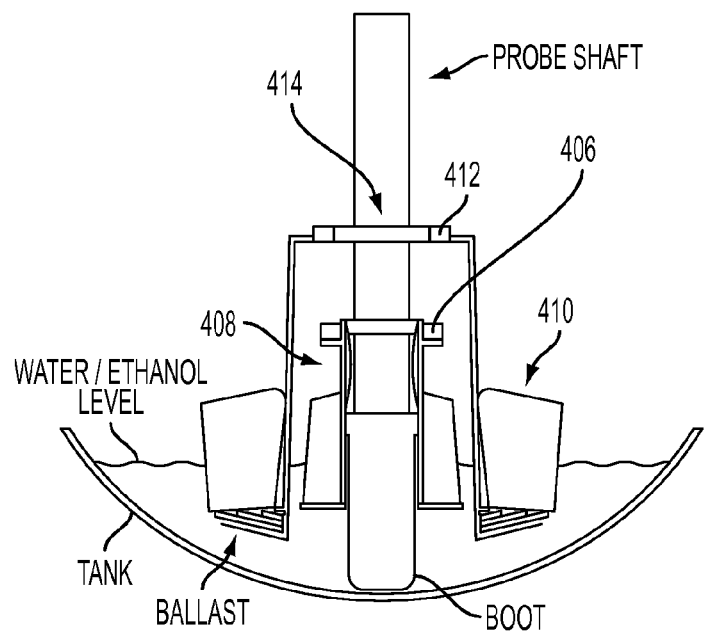
FIG. 10B is a cross-sectional view of a phase separation float assembly having a magnetic stop feature according to one embodiment of the present invention.

In a further embodiment of a phase separation float assembly similar to that illustrated in FIG. 10A, FIG. 10B illustrates an alternative stop feature which may be provided to engage inner and outer floats 408, 410, respectively. Specifically, instead of a recessed lip, a phase separation float assembly may be provided with a second magnet 412 coupled to a collar portion 414 of the outer float subassembly. The inner float subassembly 408 is arranged completely below collar portion 414 along the magnetostrictive probe shaft in this embodiment. The magnets 406, 412 coupled to the inner float subassembly 408 housing and the outer float subassembly 410 housing are preferably arranged with opposing polarity, such that that the magnets 406, 412 will repel each other when in close proximity. Thus, as the inner float subassembly 408 rises in the presence of phase separation, the magnet 406 coupled to the inner float subassembly 408 will repel the magnet 412 coupled to the outer float subassembly 410 collar portion 414. Eventually, this repelling force will cause the inner and outer float subassemblies 408, 410 to rise together to indicate the presence of phase separation. As explained above, this arrangement allows detection of a phase separation layer at a lower level than a traditional water float.

While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. A phase separation float assembly for use with a fuel level probe having a shaft extending into a fuel storage tank, said phase separation float assembly comprising:
   a first float subassembly comprising a first float adapted for vertical travel along said fuel level probe shaft and a first magnet, said first float having a first density;
   a second float subassembly comprising a second float adapted for vertical travel along said fuel level probe shaft and at least one stop feature which engages said first float subassembly when said first float subassembly travels vertically a predetermined distance along said fuel level probe shaft;
   said second float having a second density greater than said first density;
   wherein said first and second densities are selected such that:
      in the presence of either higher density phase separation or water, both of said first and second float subassemblies travel vertically along said shaft; and
      in the presence of either a higher density fuel or lower density phase separation, only said first float subassembly travels vertically along said shaft.

2. The phase separation float assembly of claim 1, wherein said fuel level probe provides information to a control system regarding the position of said first magnet along said fuel level probe shaft.

3. The phase separation float assembly of claim 2, wherein said control system is configured to interpret whether vertical travel of said first float subassembly along said fuel level probe shaft indicates the presence of phase separation.

4. The phase separation float assembly of claim 1, wherein said second float subassembly comprises a second magnet.

5. The phase separation float assembly of claim 1, wherein at least one of said first and second float subassemblies comprises at least one ballast.

6. The phase separation float assembly of claim 1, wherein said second float subassembly at least partially surrounds said first float subassembly.

7. The phase separation float assembly of claim 6, wherein said second float subassembly defines at least one window to facilitate fuel flow around said first and second float subassemblies.

8. The phase separation float assembly of claim 6, wherein said first and second float subassemblies comprise a generally cylindrical body portion.

9. The phase separation float assembly of claim 1, wherein said stop feature comprises a plurality of teeth.

10. The phase separation float assembly of claim 1, wherein said stop feature comprises a lip.

11. The phase separation float assembly of claim 1, wherein said first magnet is annular.

12. A phase separation float assembly for use with a fuel level probe having a shaft extending into a fuel storage tank, said phase separation float assembly comprising:
- a first float subassembly comprising a first float adapted for vertical travel along said fuel level probe shaft and a magnet, said first float having a first density;
- a second float subassembly comprising a second float adapted for vertical travel along said fuel level probe shaft, said second float having a second density greater than said first density; and
- said second float subassembly further comprising at least one stop feature which engages said first float subassembly when said first float subassembly travels vertically a predetermined distance along said fuel level probe shaft;
- wherein said first float density is selected such that said first float subassembly travels vertically along said shaft to engage said at least one stop feature in the presence of phase separation.

13. The phase separation float assembly of claim 12, wherein said second float subassembly at least partially surrounds said first float subassembly.

14. The phase separation float assembly of claim 12, wherein both of said first and second float subassemblies travel vertically along said fuel probe shaft in the presence of higher density phase separation or water.

15. The phase separation float assembly of claim 12, wherein said second float density is selected such that said second float subassembly does not travel vertically along said fuel level probe shaft in the presence of a higher density fuel or lower density phase separation.

16. The phase separation float assembly of claim 12, wherein the density of said first float is selected such that said first float subassembly also travels vertically along said shaft to engage said at least one stop feature in the presence of a higher density fuel.

17. The phase separation float assembly of claim 12, wherein said first and second float subassemblies comprise a base portion having at least one aperture therethrough to allow fluid flow around said first and second float subassemblies.

18. The phase separation float assembly of claim 12, wherein said fuel level probe provides information to a control system regarding the position of said magnet along said fuel level probe shaft.

19. The phase separation float assembly of claim 18, wherein said control system is configured to interpret whether vertical travel of said first float subassembly along said fuel level probe shaft indicates the presence of phase separation.

20. The phase separation float assembly of claim 12, wherein the density of said first float subassembly is approximately equal to 790 kg/m$^3$.

21. The phase separation float assembly of claim 12, wherein the density of said second float subassembly is approximately equal to 820 kg/m$^3$.

22. The phase separation float assembly of claim 12, wherein the combined density of said first and second float subassemblies is approximately equal to 810 kg/m$^3$.

23. A method for detecting phase separation in a fuel storage tank comprising the steps of:
- providing a first float subassembly comprising a first float adapted for vertical travel along a shaft of a fuel level probe and a magnet;
- providing a second float subassembly comprising a second float adapted for vertical travel along said fuel level probe shaft and at least one stop feature which engages said first float subassembly when said first float subassembly travels vertically a predetermined distance along said fuel level probe shaft;
- evaluating the position of said first float subassembly along said fuel level probe shaft using said magnet; and
- determining whether said first float subassembly has traveled a distance greater than said predetermined distance.

24. The method of claim 23, wherein said second float subassembly at least partially surrounds said first float subassembly.

25. The method of claim 23, further comprising communicating said first float assembly position information to a control system.

26. The method of claim 23, further comprising determining whether said position of said first float subassembly along said fuel level probe shaft indicates the presence of phase separation.

27. The method of claim 26, further comprising evaluating temperature and density information regarding one or more fluids in said fuel storage tank.

28. The method of claim 26, further comprising disabling a fuel pump associated with said fuel storage tank if the presence of phase separation is indicated.

29. The method of claim 23, further comprising determining whether both first and second float subassemblies have traveled vertically along said fuel level probe shaft.

30. The method of claim 23, further comprising evaluating the rate of change of said position of said first float subassembly along said fuel level probe shaft.

31. A fuel level probe for measuring the height of one or more fluids in a fuel storage tank, said fuel level probe comprising:
- a shaft extending into said fuel storage tank, said shaft comprising a ferromagnetic wire;
- control electronics in electrical communication with said ferromagnetic wire to generate an interrogation pulse along said ferromagnetic wire;
- a first float subassembly comprising a first float adapted for vertical travel along said fuel level probe shaft, said first float having a first density;
- said first float subassembly further comprising a magnet which causes a torsional wave in said ferromagnetic wire in response to said interrogation pulse;
- a second float subassembly comprising a second float adapted for vertical travel along said fuel level probe shaft, said second float having a second density greater than said first density;
- said second float subassembly further comprising at least one stop feature which engages said first float subassembly when said first float subassembly travels vertically a predetermined distance along said fuel level probe shaft;
- wherein said first float density is selected such that said first float subassembly travels vertically along said shaft to engage said at least one stop feature in the presence of phase separation.

32. The fuel level probe of claim 31, wherein both of said first and second float subassemblies travel vertically along said fuel probe shaft in the presence of higher density phase separation or water.

33. The fuel level probe of claim 31, wherein said second float density is selected such that said second float subassembly does not travel vertically along said fuel level probe shaft in the presence of a higher density fuel or lower density phase separation.

34. The fuel level probe of claim 31, wherein the density of said first float is selected such that said first float subassembly also travels vertically along said shaft to engage said at least one stop feature in the presence of a higher density fuel.

35. The fuel level probe of claim 31, wherein said fuel level probe shaft is coupled with a boot.

36. The fuel level probe of claim 31, wherein said fuel level probe provides information to a control system regarding the position of said magnet along said fuel level probe shaft.

37. The fuel level probe of claim 36, wherein said control system is configured to interpret whether vertical travel of said first float subassembly along said fuel level probe shaft indicates the presence of phase separation.

38. The fuel level probe of claim 31, further comprising a density meter coupled with said fuel level probe shaft.

39. A phase separation detection system for detecting phase separation in a fuel storage tank, said phase separation detection system comprising:
- a fuel level probe comprising a shaft extending into said fuel storage tank;
- a control system in electronic communication with said fuel level probe;
- a first float subassembly comprising a first float adapted for vertical travel along said fuel level probe shaft and a first magnet;
- a second float subassembly comprising a second float adapted for vertical travel along said fuel level probe shaft; and
- said second float subassembly further comprising at least one stop feature which engages said first float subassembly when said first float subassembly travels vertically a predetermined distance along said fuel level probe shaft;
- wherein the respective densities of said first and second floats are selected such that, in the presence of phase separation, said first float subassembly travels vertically along said shaft to engage said at least one stop feature.

40. The phase separation detection system of claim 39, wherein said fuel level probe provides information to said control system regarding the position of said first magnet along said fuel level probe shaft.

41. The phase separation detection system of claim 40, wherein both of said first and second float subassemblies travel vertically along said fuel probe shaft in the presence of higher density phase separation or water.

42. The phase separation detection system of claim 40, wherein the density of said first float is selected such that said first float subassembly also travels vertically along said shaft to engage said at least one stop feature in the presence of a higher density fuel.

43. The phase separation detection system of claim 42, wherein said second float density is selected such that said second float subassembly does not travel vertically along said fuel level probe shaft in the presence of a higher density fuel or lower density phase separation.

44. The phase separation detection system of claim 39, further comprising at least one temperature probe positioned in said fuel storage tank and in operative communication with said control system.

45. The phase separation detection system of claim 44, wherein said control system utilizes temperature information regarding one or more fluids in said fuel storage tank to determine whether phase separation is present.

46. The phase separation detection system of claim 39, wherein said control system utilizes density information regarding one or more fluids in said fuel storage tank to determine whether phase separation is present.

47. The phase separation detection system of claim 39, wherein said control system evaluates the rate of change of the position of said first magnet along said fuel level probe shaft to determine whether phase separation is present.

48. The phase separation detection system of claim 39, wherein said control system disables a fuel pump associated with said fuel storage tank if it determines that phase separation is present.

49. The phase separation detection system of claim 39, wherein said second float subassembly comprises a second magnet.

50. The phase separation detection system of claim 49, wherein said control system utilizes information regarding the relative positions of said first and second magnets along said fuel level probe shaft to determine a density of a fluid in said fuel storage tank.

* * * * *